United States Patent [19]

Shimonaka et al.

[11] Patent Number: 4,794,913
[45] Date of Patent: Jan. 3, 1989

[54] SUCTION CONTROL UNIT FOR AN ENDOSCOPE

[75] Inventors: Hideki Shimonaka; Yosuke Yoshimoto; Masaaki Nakazawa, all of Hachioji, Japan

[73] Assignee: Olympus Optical Co., Ltd., Japan

[21] Appl. No.: 127,379

[22] Filed: Dec. 2, 1987

[30] Foreign Application Priority Data

Dec. 4, 1986 [JP] Japan .................. 61-289294

[51] Int. Cl.⁴ .................................... A61B 1/00
[52] U.S. Cl. .................................... 128/4
[58] Field of Search .................................... 128/4

[56] References Cited

U.S. PATENT DOCUMENTS

| | | | |
|---|---|---|---|
| 4,412,531 | 11/1983 | Chikashige | 128/4 |
| 4,469,090 | 9/1984 | Konomura | 128/4 |
| 4,537,209 | 8/1985 | Sasa | 128/4 X |
| 4,561,428 | 12/1985 | Konomura | 128/4 |
| 4,736,732 | 4/1988 | Shimonaka et al. | 128/4 |

*Primary Examiner*—William H. Grieb

[57] ABSTRACT

In a suction control unit used with an endoscope having a channel, a tubular main body has a suction port in the side wall and a bore and in the bore, an inner tube with a through hole communicating with the channel of the endoscope is installed. A sliding tube is located slidably in the axial direction between the main body and the inner tube. The proximal end portion of an operating lever is secured at an upper position of the sliding the tube while the distal end portion extends outside the main body. This suction control unit is equipped with passage switching unit to connect the suction port with the endoscope channel or the outside of the main body through a relief port when the operating lever is operated.

8 Claims, 8 Drawing Sheets

SUCTION CONTROL UNIT FOR AN ENDOSCOPE

BACKGROUND OF THE INVENTION

A. Field of the Invention

This invention relates to a suction control unit for an endoscope, which can switch over from one passage to another in the endoscope.

B. Description of the Prior Art

A typical suction control unit for an endoscope is disclosed in Japanese Utility Model Publication No. 81-9941.

This suction control unit is fitted in the opening portion of an endoscope, through which a treating instrument can be inserted into a body cabity. In this suction control unit, a cylindrical main body is connected to a forceps channel through which forceps or the like is inserted, a suction port communicating with the suction unit is cut in the middle portion of the side wall of the main body, and a cylinder is fixed inside the main body. A sliding valve for opening and closing the suction port is provided in the cylinder. The valve is normally open, having the opening of the main body communicate with the suction unit, thus lightening the load on a suction pump of the suction unit. To draws the filth or the like from the abdominal cavity through the forceps channel, closes the opening of the main body with his finger.

In the suction control unit disclosed in Japanese Utility Model Disclosure (Kokai) No. 85-23001, a valve seat is formed on the bottom of a cylindrical main body, and an elastic valve member is provided in the main body.

However, the problem with the above suction control unit is that the operator has to close the opening (relief port) with his finger in a suction operation, and that filth substances drawn up from the abdominal cavity through the forceps channel flows to the relief port, thus smearing the operator's finger, which is unhygienic.

SUMMARY OF THE INVENTION

The object of this invention is to provide a suction control unit for an endoscope, which is free from the problem that the operator's finger is smeared by filthy substances spurting from the relief port in suction operation.

The object of this invention can be achieved by a suction control unit which will be described in the following. This suction control unit is used with an endoscope having a channel. The suction control unit has a suction port cut in a side wall, a tubular main body having a bore, and an inner tube located in the bore and having an internal hole communicating with the channel of the endoscope. A sliding tube is installed between the main body and the inner tube and can slide in the axial direction. The proximal end portion of an operating lever is secured to an upper position of the sliding tube and the other end portion extends outside the main body. The suction control unit is equipped with a passage-switching unit to connect the suction port with the endoscope channel or the outside of the main body through the relief port by moving the sliding tube in the axial direction with the operating lever.

The suction control unit for an endoscope according to this invention permits the operator to switch over one passage for suction to another, by putting the operating members into action without touching the relief port.

Therefore, there is no possibility that the operator's finger is smeared by filthy substances spouting from the relief port when the substances are drawn from the body cavity into the endoscope. Hence, this invention enables a hygienic handling of an endoscope.

DETAILED DESCRIPTION OF THE PREFERRED EMBODIMENTS

The preferred embodiments of this invention will now be described with reference to the accompanying drawings.

Figure 1:
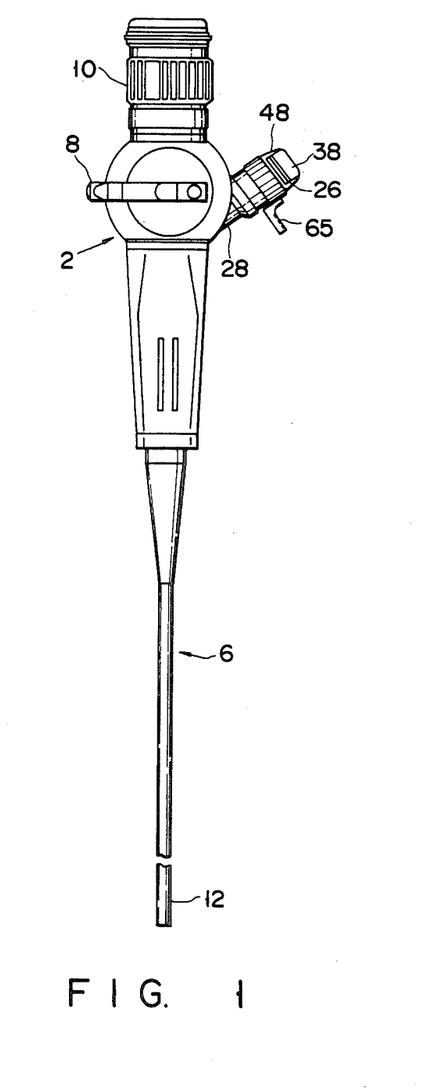
FIG. 1 is a side view showing the whole of an endoscope incorporating a suction control unit according to this invention.

FIG. 1 shows an overall view of an endoscope, that is, a fiberscope. This endoscope comprises operation section 2 and insertion section 6. Operating section 2 has angle knob 8 and eyepiece 10. Insertion section 6 has at its end bending portion 12, which can be bent by manipulating angle knob 8 and thereby it is possible to observe the condition in the abdominal cavity through eyepiece 10 of operating section 2. Eyepiece 10 has photo sensor 14 built therein which is used to set an adequate exposure value of an image pickup unit (not shown).

Figure 2:
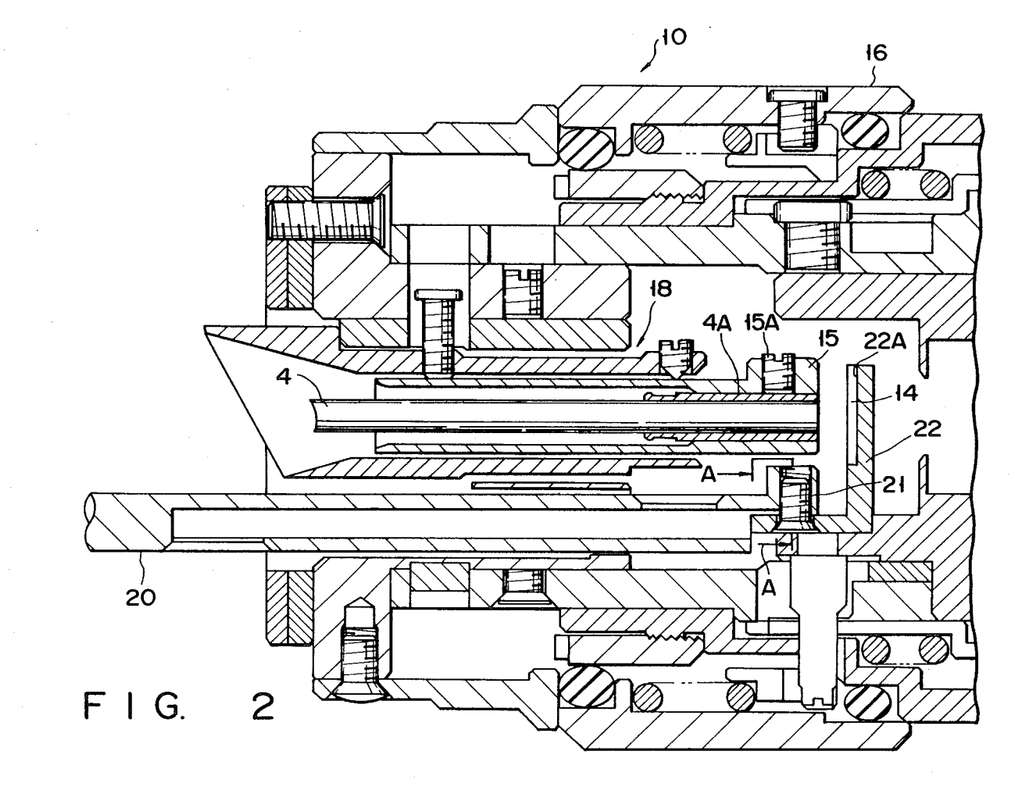
FIG. 2 is a longitudinal sectional view showing the internal construction of the eyepiece of the endoscope of FIG. 1.
Figure 3:
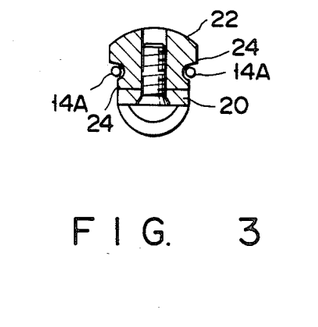
FIG. 3 is a sectional view taken along line A—A of FIG. 2.

Referring to FIGS. 2 and 3, description will now be made of the construction of eyepiece 10 with a built-in photo sensor. Image guide fiber 4 is installed about the center of eyepiece 10 and proximal end portion 4A of image guide fiber 4 is fixed in mounting member 15 by means of screw 15A. Diopter control ring 16 is mounted at the outermost peripheral position of eyepiece, By rotating diopter control ring 16, lens guide (not shown) can be moved forward and backward with respect to proximal end portion of image guide fiber 4. Image guide focusing device 18 is mounted around proximal end portion 4A of image guide fiber 4. Swing shaft 20 to move photo sensor 14 is arranged in parallel with image guide fiber 4. The distal end portion (not shown) of swing shaft 20 is coupled to the operating handle (not shown) to swing shaft 20. L-shaped member 22 is fastened with set screw 21 at the proximal end portion of swing shaft 20. Photo sensor 14 is set in recessed part 22A of L-shaped member 22. By moving swing shaft 20 with the operating handle, photo sensor 14 is placed between the proximal end face of image guide fiber 4 and the lens unit (not shown), and the light receiving face of photo sensor 14 is placed facing the proximal end face of image guide fiber 4. When an exposure value has been measured, swing shaft 20 is moved in the opposite direction and thereby photo sensor 14 is removed from between the proximal end face of image guide fiber 4 and the lens unit.

As shown in FIG. 3, cords 14A connected to photo sensor 14 are glued and fastened in grooves 24 formed in the axial direction on both sides of swing shaft 20. Both ends of cords 14A are connected to imaging control circuit (not shown) provided externally. As has been described, this endoscope is capable of detecting an exposure value by the use of photo sensor 14.

Figure 4:
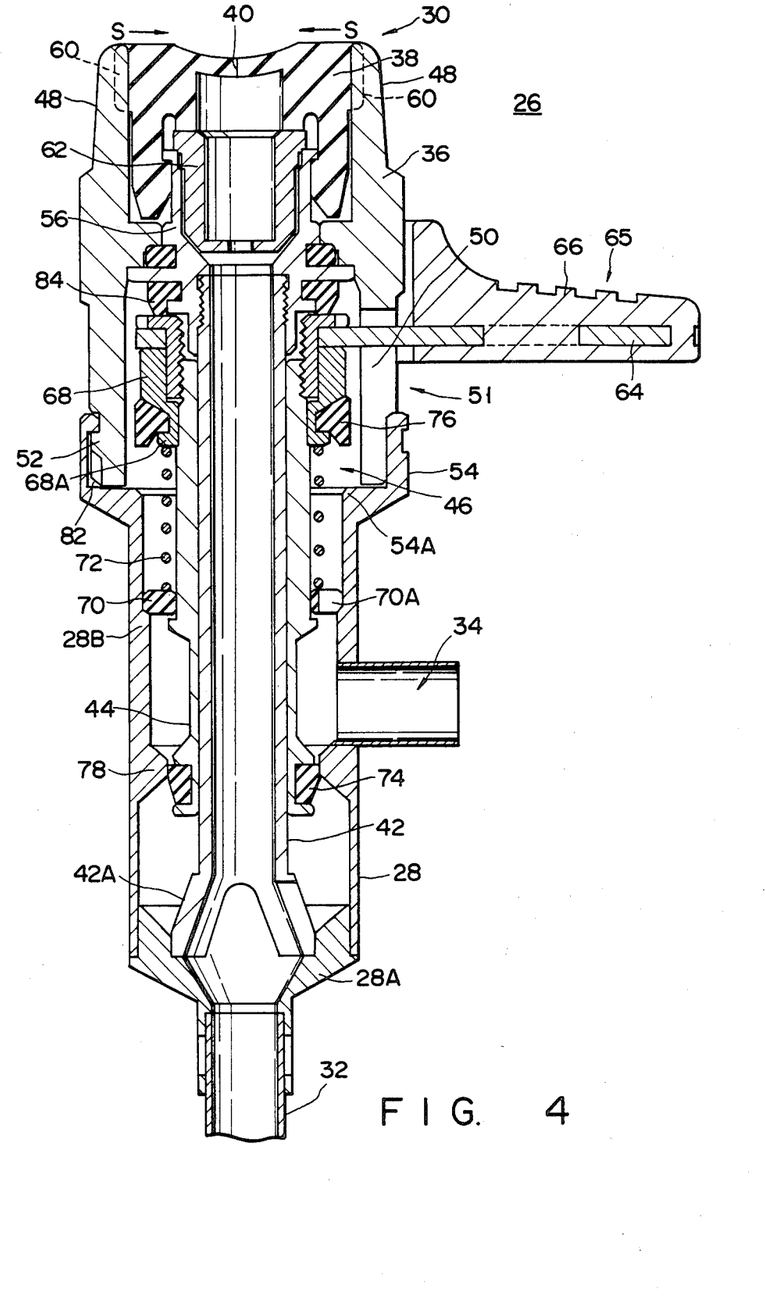
FIGS. 4 and 5 are longitudinal sectional views showing the suction control unit according to the first embodiment of this invention.
Figure 5:
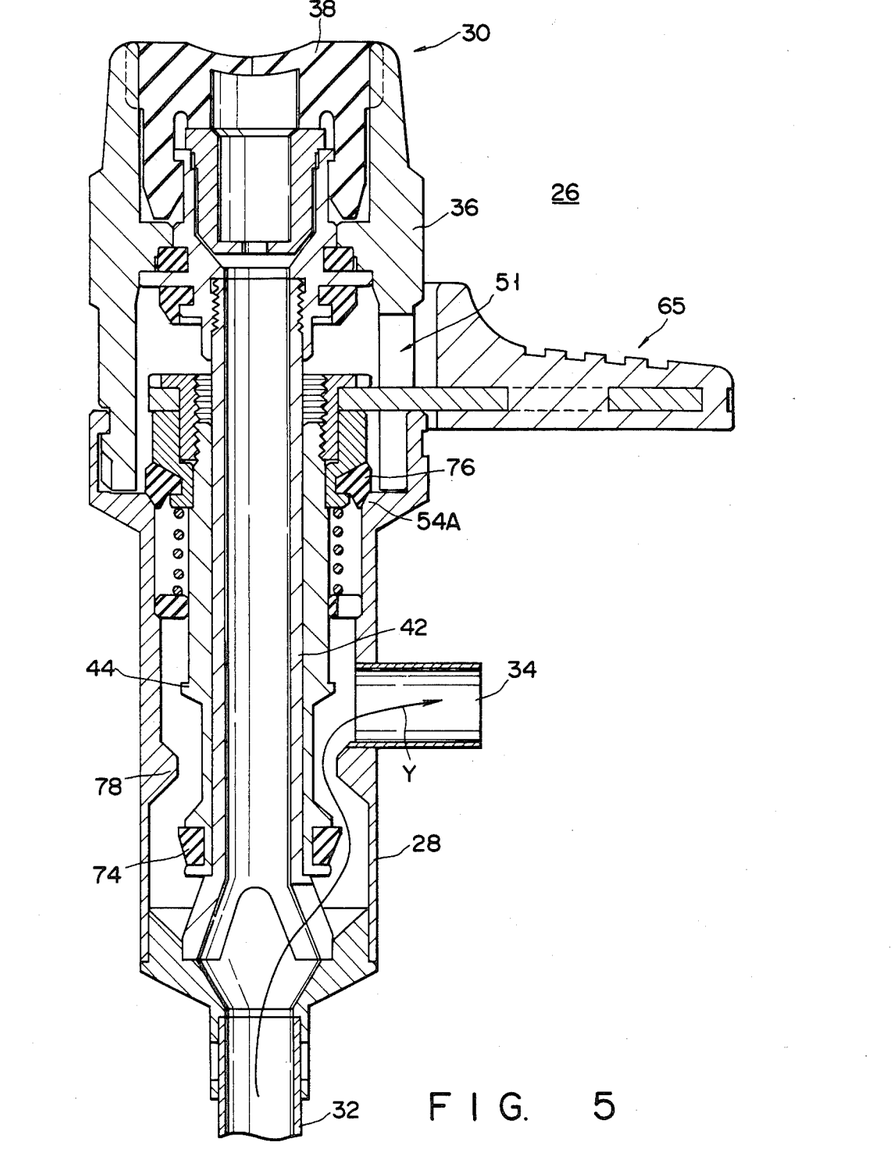

Suction control unit 26 according to this invention will now be described with reference to FIGS. 4 and 5. Suction control unit 26 has a tubular body, that is, outer tube 28 mounted on operating section 2, and working unit 30 removably provide in outer tube 28. Nearly conical outer tube seat 28A is attached to the bottom part of outer tube 28. To the lower end part of outer tube seat 28, forceps channel 32 is coupled. Suction port 34 which communicates with a suction pump (not shown) as a suction source is formed at the wall of the intermediate part of exposed outer tube 28.

Working unit 30 comprises housing 36, elastic plug 38 having slit 40, inner tube 42 communicating with channel tube 32 and sliding tube 44. Housing 36 having a tubular form is provided with a pair of projected parts for mounting the elastic plug at its upper portion and notched part serving as relief port 51 in its lower wall. Housing 36 also has stoppers 52 formed projecting at two positions at the lower-end periphery formed with a relatively smaller diameter. Using stoppers 52, housing 36 can be secured to large-diameter portion 54 formed at the opening of outer tube 28.

Inner tube 42 has distal end portion 42A which is divided into two parts. The upper end portion of inner tube 42 is held by supporting member 56 installed in housing 36, and the lower end portion of inner tube 42 is accommodated in outer tube 28. The lower end portion of inner tube 42 communicates with forceps channel 32 and the upper end opening of inner tube 42 communicates with the outside of housing 36.

Figure 6:
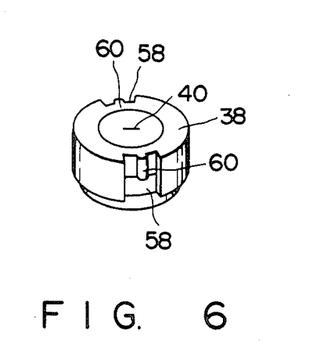
FIG. 6 is a perspective view of the elastic plug in the working unit.

As shown in FIG. 6, elastic plug 38 has in its periphery recessed parts 58 formed which engage with projected parts 48 of housing 36. Elastic plug 38 is removably fitted in the space between projected parts 48 which communicates with inner tube 42. Therefore, it is possible to insert forceps (not shown) or supply a liquid into forceps channel 32 through slit 40 formed at the center of elastic plug 38. Projection 60 is formed integrally with elastic plug 38 on the inner bottom face of each recessed part 58 thereof. The object of these projections is to cause elastic plug 38 to be deformed to press slit 40 from two sides when elastic plug 38 is fitted into housing 36, that is to say, to deform elastic plug 38 by pressing the plug in the directions of the arrows S indicated in FIG. 4, thereby improving the airtightness of slit 40. Coupling member 62 is attached to the opening of supporting member 56 and constitutes the mounting seat for elastic plug 38.

Sliding tube 44 constituting flow passage changeover device 46 is mounted slidably in the axial direction on the outer periphery of inner tube 42. The proximal end portion of lever plate 64 is mounted at the upper part of sliding tube 44 and is secured by lever fixing member 68. Lever plate 64 passes through notched part 50 of housing 3 and the other end portion projects outside from housing 36. Finger-operation knob 66 constituting operating lever 65 is secured to the periphery of the other end portion of lever plate 64.

Spring seat 70 is mounted movably in the axial direction on the periphery of the middle position of sliding tube 44. Notch 70A is formed at the periphery of spring seat 70. Coil spring 72 is placed between spring seat 70 and spring seat portion 68A of lever fixing member 68. When inner tube 42 is inserted into outer tube 28, spring seat 70 is stopped by stepped portion 28B formed at the middle position of outer tube 28. After inner tube 42 has been fitted into outer tube 28, sliding tube 44 and operating lever 65 are pressed upward by the force of coil spring 72.

Annular elastic valve members 74 and 76 are mounted to the outer periphery of distal end portion of sliding tube 44 and lever fixing member 68, respectively. Valve seat 78 is formed just below suction port 34 on the inner periphery of outer tube 28. First elastic valve member 74 is in close contact with valve seat 78 before operating lever 65 is operated. Second elastic valve member 76 comes into close contact with stepped part 54A of large-diameter portion 54 when operating lever 65 is pushed downward. More specifically, before operating lever 65 is operated, as shown in FIG. 4, first passage communicating between suction port 34 and forceps channel 32 is closed. At the same time, second passage running from suction port 34 through notch 70A, large-diameter portion 54 and relief port 51 to the outside is open. As shown in FIG. 5, when operating lever 65 is pushed, second passage is closed and first passage is open.

Figure 7:
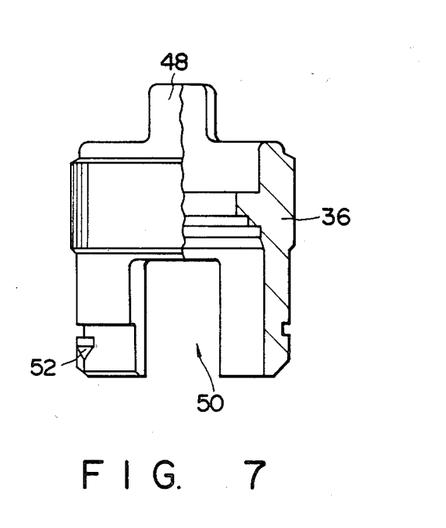
FIGS. 7 and 8 are a partly-sectional side view and a bottom end view of the housing in the working unit.
Figure 8:
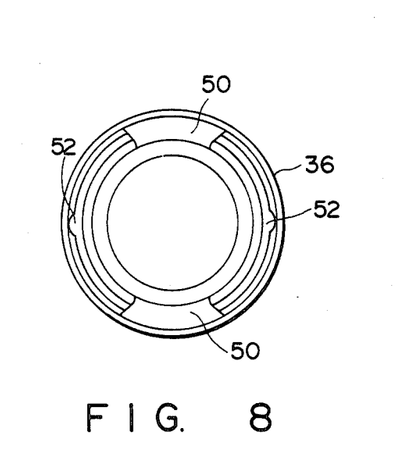
Figure 9:
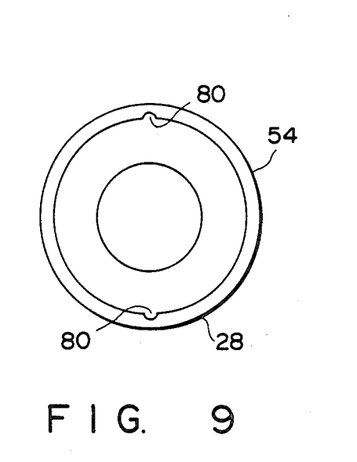
FIG. 9 is a plan view of the outer tube.

Referring to FIGS. 7 through 9, description will now be made of the structure for fixing working unit 30 to outer tube, namely, main body 28. Formed on the inner periphery of large-diameter portion 54 of main body 28 is a pair of grooves 80 for receiving stoppers 52 of housing 36. At the deep ends of grooves 80, there are holding grooves 82 (shown in FIG. 4) to guide stoppers 52 in the circumferential direction. With stoppers 52 inserted in grooves 80, by turning housing 36 about 90 degrees to guide stoppers 52 into holding grooves 82, housing 36 can be attached to main body 28. On the other hand, by turning housing 3 about 90 degrees in the opposite direction and pulling it out, the whole working unit can be detached from main body 28. Meanwhile, placed at a lower position of supporting member 56 is cushion material 84 to lessen an impact which will otherwise occur when operating lever 65 hits on supporting member 56

As set forth above, the whole body of the suction control unit according to this invention is secured to operating section 2 of an endoscope under the condition that operating unit 30 is fitted to outer tube 28. This suction control unit is capable of switching over from one passage for suction to another by the use of two open/close valves, which have elastic valve members 74, 76, respectively.

Next, the operation of the suction control unit according to this invention will now be described in the following. Under the condition that working unit 30 is attached to outer tube 28, first elastic valve member 74 of sliding tube 44 is in close contact with valve sea 78 and at the same time, second elastic valve member 76 is separated from stepped part 54A of large-diameter portion 54. When operating lever 65 is pushed, first passage running from suction port 34 to forceps channel is opened and second passage running from suction port 34 to the outside is closed. As a result, filth is drawn in from the distal end of the insertion section. As indicated the arrow Y in FIG. 5, the filth enters the branched ends of inner tube 42, passes through the space between sliding tube 44 and outer tube 28, and goes into suction port 34. Therefore, the filth can be drawn in without allowing it to enter relief port 51. Hence, if an endoscope incorporating a suction control unit according to this invention, there is no possibility that the operator's fingers are smeared with filth spouting from the relief port when it is drawn out.

Figure 10:
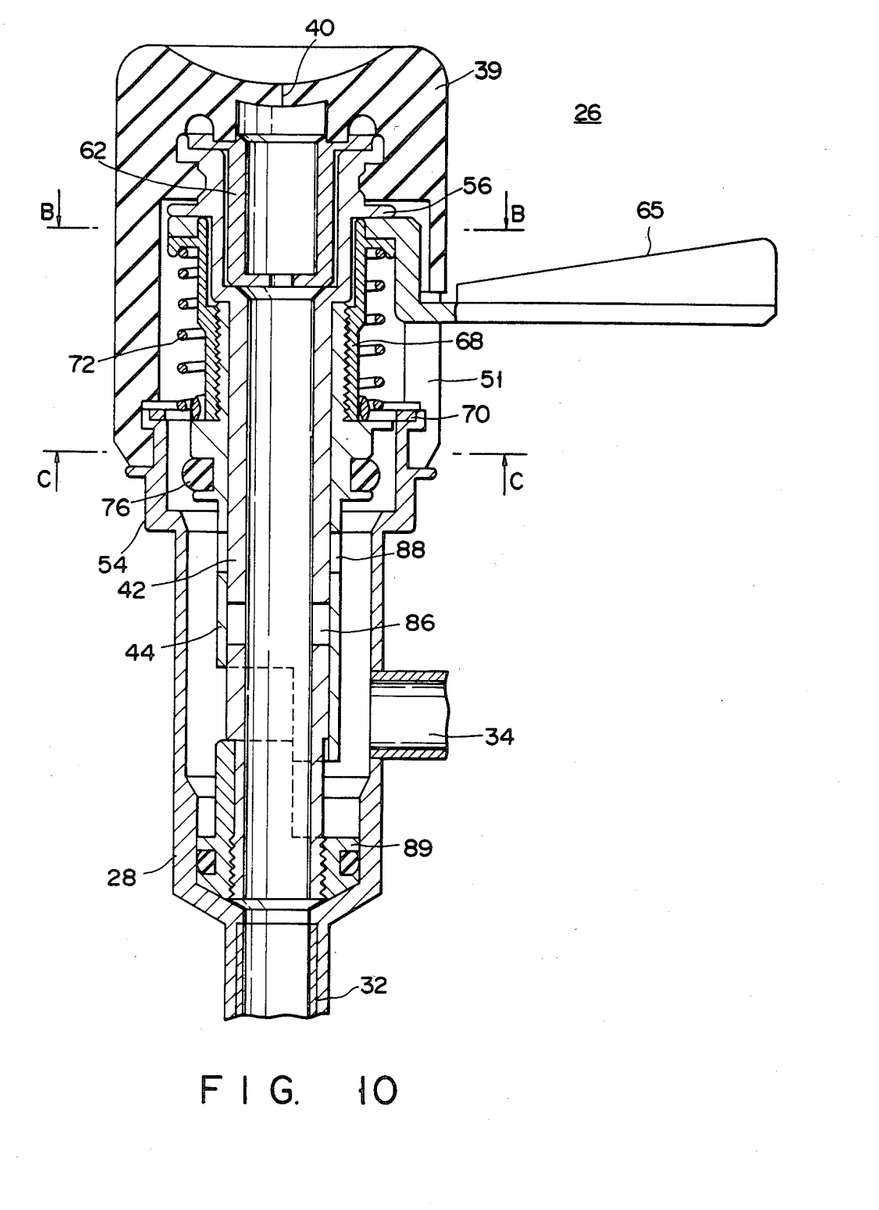
FIG. 10 is a longitudinal sectional view showing a suction control unit according to the second embodiment of this invention.
Figure 11:
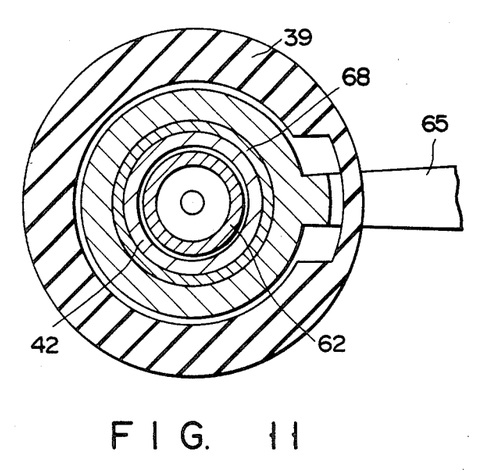
FIG. 11 is a sectional view taken along line B—B of FIG. 10.
Figure 12:
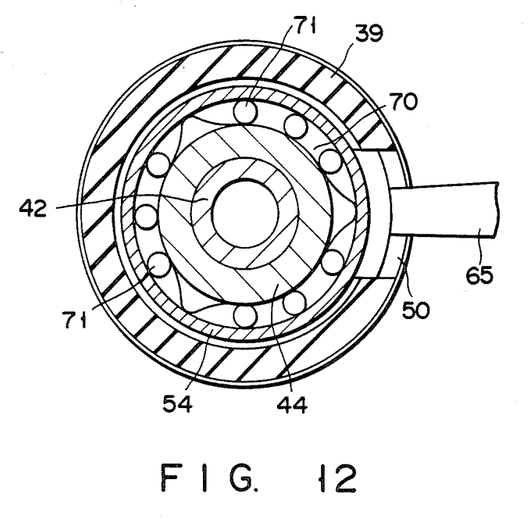
FIG. 12 is a sectional view taken along line C—C of FIG. 11.

The second embodiment of this invention will now be described with reference to FIGS. 10 through 12. The same numerals will be used for those members which have been described in the first embodiment and those members will not be described.

In this second embodiment, elastic housing 39 having slit 40 is used. Elastic housing 39 can be easily detached from outer tube 28. Ports 86, 88 are formed in inner tube 42 and outer tube 44, respectively. The flow passages can be changed over by opening and closing ports 86, 88. As shown in FIG. 12, a plurality of holes 71 are formed in spring seat 70, thereby securing a passage running from suction port 34 to relief port 51. Provided at the distal end portion of sliding tube 19 is guide member 89 which allows sliding tube 19 to move in the axial direction, but prevents sliding tube 19 to from rotating. By this means, it is possible to avoid trouble that operating lever 65 rotates when this suction control unit is operated.

Figure 13:
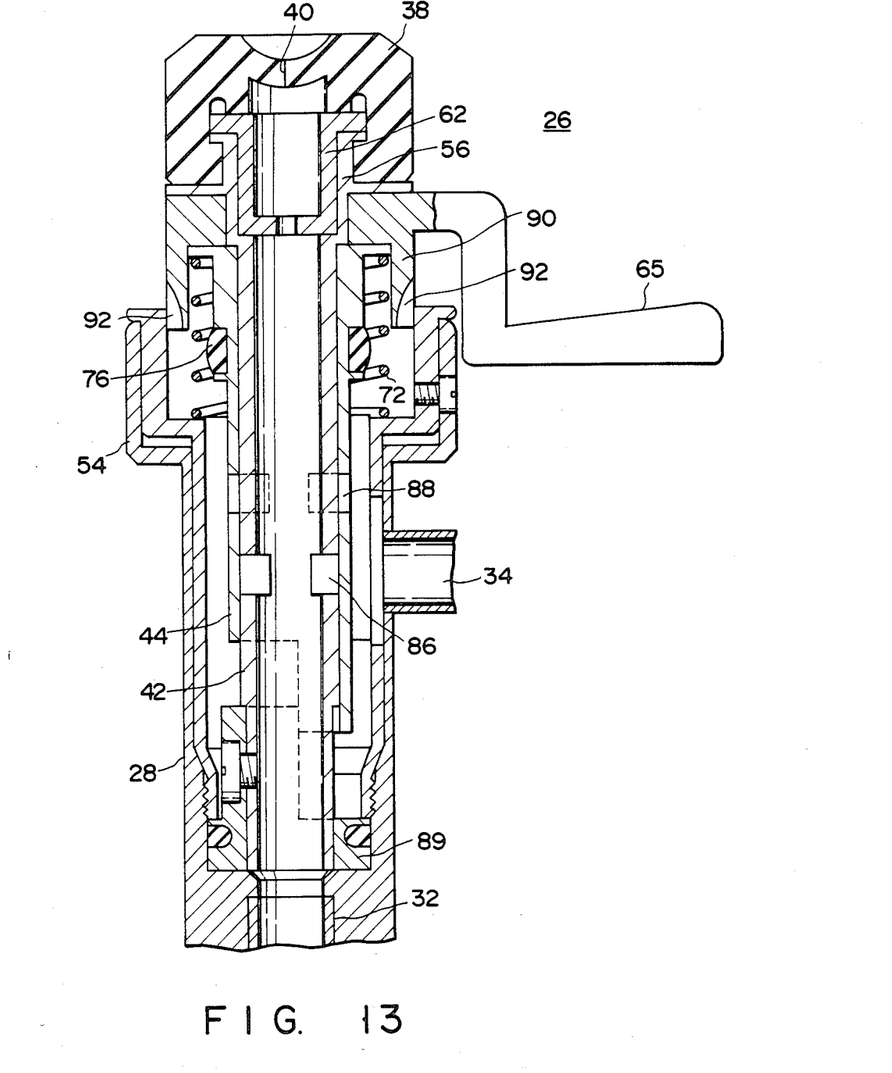
FIG. 13 is a longitudinal sectional view showing a suction control unit according to the third embodiment of this invention.

FIG. 13 shows the third embodiment according to this invention. In this third embodiment, provided at the proximal end portion of operating lever 65 is annular wall 90 which slidably engages with the opening portion of outer tube 28. A plurality of air vents serving as relief ports are provided at the outer periphery of annular wall 90. Housing 36 is not used just as in the second embodiment of this invention. The construction of the other parts is the same as in the preceding embodiments and its description is not repeated.

What is claimed is:

1. A suction control unit for an endoscope having a channel, comprising:
    a tubular main body having a suction port in the side wall and a bore;
    an inner tube located in the bore and having an internal hole communicating with the channel of the endoscope;
    a sliding tube located slidably in the axial direction between said main body and said inner tube;
    an operating lever having its proximal end portion secured at an upper position of said sliding tube and its distal end portion extending outward from said main body; and
    passage switching means for connecting the suction port with the endoscope channel or the outside of said main body, when said operating lever is operated to move said sliding tube forward or backward in the axial direction.

2. The suction control unit according to claim 1, wherein said passage switching means comprises
    first valve means for opening and closing a first passage running from the suction port to the channel, said first valve means having a first valve member attached to one end portion of said sliding tube and a first valve seat formed at on end portion of said main body; and
    second valve means for opening and closing a second passage running from the suction port to the outside of said main body, said second valve means having a second valve member attached to the other end portion of said sliding tube and a second valve seat formed at the other end portion of said main body.

3. The suction control unit according to claim 2, wherein said passage switching means comprises a spring to pressurize said sliding tube upward.

4. The suction control unit according to claim 3, further comprising: a tubular housing holding said inner tube and attached removably to the opening portion at the upper end of said main body.

5. The suction control unit according to claim 4, wherein said housing has at least two projections at its upper end, said two projections holding therebetween an elastic plug having a slit in its middle position.

6. The suction control unit according to claim 5, wherein said housing, inner tube, sliding tube, operating lever, the first and second valve members make up one unit detachable from said main body.

7. The suction control unit according to claim 1, wherein said passage switchover means comprises
    first valve means having a first port formed at one end portion of said sliding tube and a second port formed at one end portion of said inner tube and being capable of opening and closing the first passage running from the suction port to the endoscope channel; and
    second valve means having a valve member attached to the other end portion of said sliding tube and a valve seat formed at the other end portion of said main body and being capable of opening and closing the second passage running from the suction port and the outside of said main body.

8. The suction control unit according to claim 7, wherein said sliding tube comprises guide means to permit said sliding tube to move in the axial direction and to prevent said sliding tube from rotating.

* * * * *